United States Patent
Richelsoph

(10) Patent No.: US 7,963,995 B2
(45) Date of Patent: Jun. 21, 2011

(54) MINIMALLY INVASIVE SPINE IMPLANT FOR RESTORATION OF MOTION

(75) Inventor: Marc Evan Richelsoph, Memphis, TN (US)

(73) Assignee: Aesculap, Inc., Center Valley, PA (US)

( * ) Notice: Subject to any disclaimer, the term of this patent is extended or adjusted under 35 U.S.C. 154(b) by 756 days.

(21) Appl. No.: 11/664,761

(22) PCT Filed: Oct. 5, 2005

(86) PCT No.: PCT/EP2005/010713
§ 371 (c)(1),
(2), (4) Date: Jan. 18, 2008

(87) PCT Pub. No.: WO2006/037621
PCT Pub. Date: Apr. 13, 2006

(65) Prior Publication Data
US 2008/0140205 A1     Jun. 12, 2008

Related U.S. Application Data

(60) Provisional application No. 60/616,047, filed on Oct. 5, 2004.

(51) Int. Cl.
*A61F 2/44* (2006.01)
(52) U.S. Cl. .................... 623/17.13; 606/90
(58) Field of Classification Search .... 623/17.11–17.16; 606/90; *A61F 2/44*
See application file for complete search history.

(56) References Cited

U.S. PATENT DOCUMENTS

| | | | | |
|---|---|---|---|---|
| 4,834,757 A | * | 5/1989 | Brantigan | 623/17.11 |
| 5,716,413 A | * | 2/1998 | Walter et al. | 424/423 |
| 5,749,916 A | * | 5/1998 | Richelsoph | 623/17.16 |
| 5,865,848 A | * | 2/1999 | Baker | 623/17.15 |
| 6,419,706 B1 | * | 7/2002 | Graf | 623/17.16 |

(Continued)

FOREIGN PATENT DOCUMENTS

EP     1 321 115     6/2006

(Continued)

OTHER PUBLICATIONS

International Search Report for PCT/EP2005/010713; Completed Dec. 12, 2005.

(Continued)

*Primary Examiner* — Eduardo C Robert
*Assistant Examiner* — Lynnsy Schneider
(74) *Attorney, Agent, or Firm* — RatnerPrestia

(57) ABSTRACT

The present invention provides a vertebral implant comprising a wall forming two short sides (100, 101) and two elongated sides (102, 103) to define a generally elongated structure having a passageway (106) therethrough. At least one of the two elongated sides is resiliently compressible into the passageway, or resiliently expandable away from the passageway, under a force applied to the implant by movement of the spine into which the implant is placed. This resilient opposition to forces in the spine causes the device to want to return to its at-rest position, thereby aiding the spine in its return to a normal position after movement is relaxed, thereby aiding proper spine alignment. Preferably, the device comprises a flexible body having a generally loop-shaped configuration defined by the wall, wherein the wall material and thickness is selected so that the device has appropriate degrees of flexibility and strength.

19 Claims, 6 Drawing Sheets

U.S. PATENT DOCUMENTS

| | | | | |
|---|---|---|---|---|
| 6,491,724 B1* | 12/2002 | Ferree | | 623/17.11 |
| 6,613,091 B1* | 9/2003 | Zdeblick et al. | | 623/17.16 |
| 6,629,998 B1* | 10/2003 | Lin | | 623/17.11 |
| 6,979,353 B2* | 12/2005 | Bresina | | 623/17.16 |
| 6,984,247 B2* | 1/2006 | Cauthen | | 623/17.16 |
| 2002/0151976 A1* | 10/2002 | Foley et al. | | 623/17.11 |
| 2004/0010315 A1* | 1/2004 | Song | | 623/17.16 |
| 2005/0043800 A1* | 2/2005 | Paul et al. | | 623/17.15 |
| 2005/0049590 A1* | 3/2005 | Alleyne et al. | | 606/61 |
| 2006/0030943 A1* | 2/2006 | Peterman | | 623/17.11 |

FOREIGN PATENT DOCUMENTS

| | | |
|---|---|---|
| JP | 2003-210500 | 7/2003 |
| WO | WO 2004/080356 | 9/2004 |

OTHER PUBLICATIONS

European Office Action Dated Nov. 12, 2010 for European Application No. 05 794 078.5.

Japanese Office Action Dated Dec. 21, 2010 for Application JP 2007-533964.

* cited by examiner

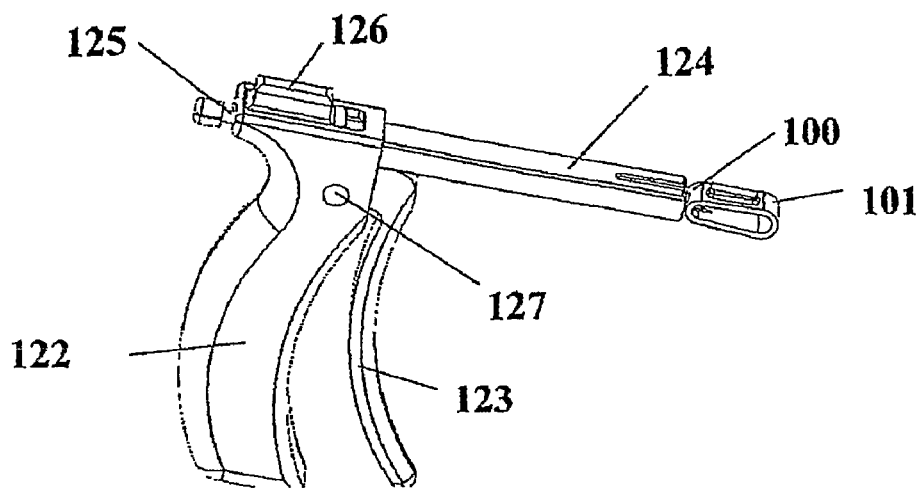
FIG. 17
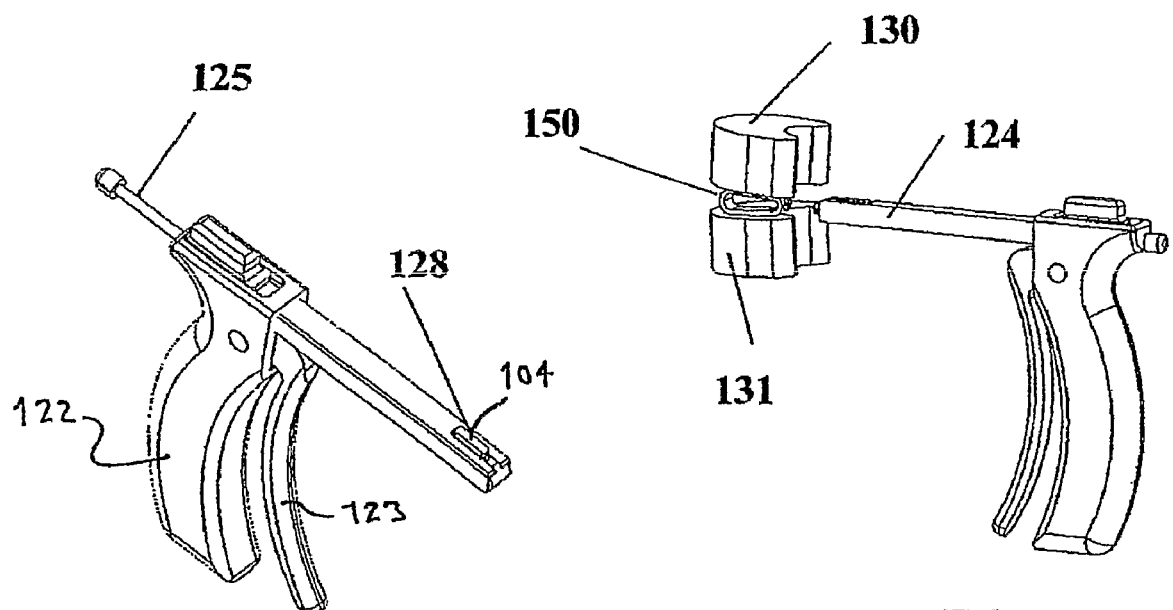
FIG. 18
FIG. 19

MINIMALLY INVASIVE SPINE IMPLANT FOR RESTORATION OF MOTION

This application is a U.S. National Phase Application of PCT International Application PCT/EP2005/010713. This application claims the benefit of Provisional Application No. 60/616,047, filed October5, 2004, titled MINIMALLY INVASIVE SPINE IMPLANT FOR RESTORATION OF MOTION which is incorporated herein in its entirety.

FIELD OF THE INVENTION

The present invention relates generally to intervertebral motion restoring implants and more specifically it relates to a minimally invasive spinal implant for restoration of motion by providing a minimally invasive implant and method for maintaining or restoring disc space height and restoring motion to a degenerated or otherwise damaged spinal disc.

BACKGROUND OF THE INVENTION

Intervertebral implants for restoration of motion have been in use for years. Typically, intervertebral motion implants are comprised of artificial discs. Prosthetic disc nucleus devices have also been used.

The main problems with artificial discs involve the complexity and difficulty of the implantation. Current artificial disc technologies use a polymer core type design or a bearing design such as metal on metal, ceramic on ceramic, or polyethylene on metal. Most or all of these implants generate wear particulate which may create long term osteolysis or other biological problems. With younger patients being treated for spine related issues, wear debris, and the potential resultant bone and tissue damage, become important issues. In addition, revision should be an important criteria as all implants are subject to needing replacement. Unfortunately, conventional artificial disc implants are extremely difficult to revise, if not impossible.

SUMMARY OF THE INVENTION

The present invention provides a vertebral implant comprising a wall forming two short sides and two elongated sides to define a generally elongated structure having a passageway therethrough. At least one of the two elongated sides is resiliently compressible into the passageway, and/or is resiliently expandable away from the passageway, under a force applied to the implant by movement of the spine into which the implant is placed. The side or sides which are compressible is moveable back to an at-rest position when the force is removed.

The present invention more specifically includes a vertebral implant comprising a wall forming a two rounded sides and two elongated straight sides to define a generally elongated structure having a passageway therethrough, with one rounded short side being larger than the other rounded short side, so that the two elongated straight sides are not parallel. In this embodiment, at least one of the two elongated sides is resiliently compressible into the passageway, or resiliently expandable away from the passageway, under a force applied to the implant by movement of the spine into which the implant is placed. In this embodiment, as above, the side which is compressed or expanded under force returns to an at-rest position when the force is removed.

Also included as a part of the present invention is a method of treating a spine, comprising the steps of providing a vertebral implant, the implant having a wall forming two short sides and two elongated sides to define a generally elongated structure having a passageway therethrough and at least one of the two elongated sides being resiliently compressible into the passageway, or resiliently expandable away from the passageway, under a force applied to the implant by movement of the spine into which the implant is placed, the at least one side returnable to an at-rest position when the force is removed. The method includes the steps of compressing the implant by applying a compressive force against at least one of the elongated sides, placing the implant between two adjacent vertebrae, and releasing the compressive force to thereby allow the implant to expand between the two adjacent vertebrae.

BRIEF DESCRIPTION OF THE DRAWINGS

The features of the invention believed to be novel and the elements characteristic of the invention are set forth with particularity in the appended claims. The figures are for illustration purposes only and are not necessarily drawn to scale. The invention itself, however, both as to organization and method of operation, may best be understood by reference to the detailed description which follows taken in conjunction with the accompanying drawing in which:

FIG. 17 is a perspective view of an embodiment of an insertion tool in accordance with the present invention with an implant in accordance with the invention partially inserted;

FIG. 18 is a perspective view of an embodiment of an insertion tool in accordance with the present invention with an implant in accordance with the invention inserted; and FIG. 19 is a perspective view of an embodiment of the present invention after insertion into a vertebral space.

DETAILED DESCRIPTION OF THE INVENTION

The present invention provides a vertebral implant comprising a wall forming two short sides and two elongated sides to define a generally elongated structure having a passageway therethrough. At least one of the two elongated sides is resiliently compressible into the passageway, or resiliently expandable away from the passageway, under a force applied to the implant by movement of the spine into which the implant is placed. The exact movement of the side or sides is dependent upon the particular physical movement of the spine. This resilient opposition to forces in the spine causes the device to want to return to its at-rest position, thereby aiding the spine in its return to a normal position after movement is relaxed, thereby aiding proper spine alignment. Preferably, the device comprises a flexible body having a generally loop-shaped configuration defined by the wall, wherein the wall material and thickness is selected so that the device has appropriate degrees of flexibility and strength.

A preferred embodiment, which will be discussed in more detail below, has an elongated structure with upper and lower surfaces for contact with vertebral end plates, and rounded first and second ends. In one embodiment, two rounded ends are not the same size, but rather are formed so that the implant has a downward slope in the anterior to posterior direction (i.e., the anterior end is larger). In a preferred embodiment, at least one protrusion extends from one of the contact surfaces.

Also in a preferred embodiment, means for releasable connection of the implant to an insertion device are provided. Various such means are contemplated as a part of the invention and they will be discussed in more detail below.

Figure 1:
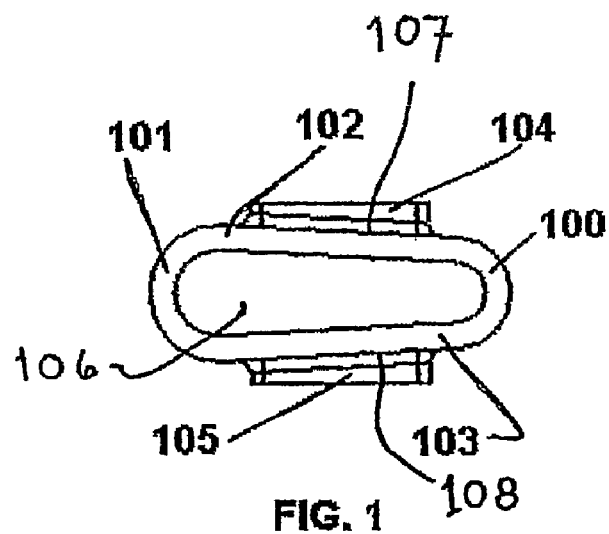
FIG. 1 is a side view of one embodiment of the present invention.
Figure 5:
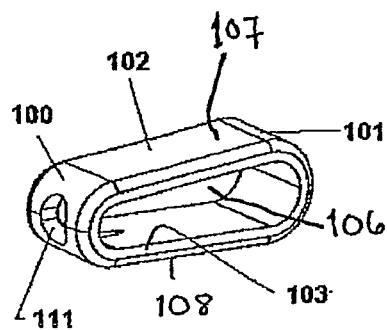
FIG. 5 is a perspective view of another embodiment of the present invention with no protrusions.

Turning now to the Figures and a specific description thereof, exemplary embodiments of the present invention are shown, for example, in FIG. 1 or FIG. 5. As shown in these embodiments, a device according to the invention comprises an elongated body defined by a wall shaped to have first end 101, second end 100, upper section 102 and lower section 103. The wall defines a device having an open passageway 106 disposed therethrough. Preferably, the short ends 100 and 101 are curved, providing an overall loop-shaped (or partially oval-shaped, with flat upper and lower sections) configuration. Other embodiments could be envisioned, however, such as devices having various degrees of curved ends (different radii of curvature), or even generally square ends to form more of a rectangular-shaped device. The importance of the selected configuration of the ends will be addressed below, as it relates to the compression resistance of the device as a whole. Generally, however, first and second ends 101 and 100, respectively, provide support to the upper and lower sections 102 and 103, while allowing controlled motion of the upper section relative to the lower section.

Figure 3:
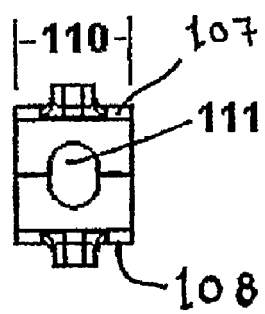
FIG. 3 is a rear view of an embodiment of the present invention.
Figure 2:
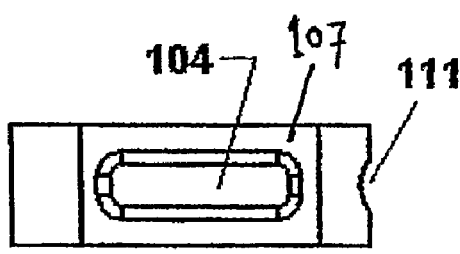
FIG. 2 is a top view of an embodiment of the present invention.
Figure 8:
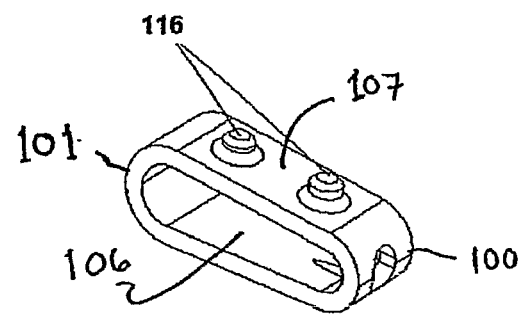
FIG. 8 is a perspective view of an embodiment of the present invention with bone contacting protrusions for bone engagement.

Upper and lower sections 102 and 103 each have vertebrae contacting outer surfaces 107 and 108. FIG. 1 illustrates an embodiment where elongated protrusions 104 and 105 extend from upper and lower surfaces 107 and 108 respectively, to aide in the securement of the device between adjacent vertebrae. FIG. 8, for example, illustrates two generally cylindrical protrusions 116 extending from upper surface 107. Other types and numbers of protrusions could be envisioned by one skilled in the art. FIG. 3 shows an end view of the device shown in FIG. 2, with instrument receiving hole 111 disposed on second end 100. As can be seen from FIG. 3, this embodiment of the implant has a relatively narrow width, indicated as width 110. FIG. 2 is a top view looking down at an embodiment of the invention having protrusion 104 and instrument receiving hole 111.

The implants of the present invention are preferably formed from a single piece of material, allowing for the creation of an implant that allows expansion and collapse of the upper section relative to the lower section in a controlled rate and manner. In effect, the elongated shape provides a means of creating an adjustable spring. By altering the wall thickness 112 of the implant, the stiffness of the implant is directly affected. This wall thickness can be uniform or vary across different sections of the implant. Thus, by so selecting the wall thickness throughout the device, a user and adjust the implant to match specific patient requirements. Depending on the design, the upper and lower sections could both be compressed equally into the passageway, or one could be compressed more as compared to the other, such as where the latter is thicker. In any event, however, the resistance of the device to compressive or expansive forces allows for a spring-like, or mechanically biased, return to its at-rest state.

Under physiological loading, motion in the spine causes the implant of the invention to expand or collapse according to this load. This allows motion in most directions, but not as much rotationally. Therefore, this method of treating spine disc degeneration or disease is primarily intended as a means to restore most function via a minimally invasive approach. In addition, such an approach allows motion restoring treatment for patients which previously would have been treated by fusion. Facet joint degeneration or damage which would heretofore have eliminated non-fusion artificial disc treatments, can now be treated by the present invention, as forces to the facet joints in rotation are controlled. In addition, the disc space is restored to the proper height, thereby reducing damaging loads to the facet joints.

The implant of the present invention is also highly beneficial for patients undergoing microdiscectomy. Microdiscectomy, along with other treatments whereby a portion of a bulging annulus or leaking nucleus is removed, can lead to disc space collapse over time. Removal of a portion of the nucleus removes support of the disc space height. However, inserting one or more of the implants of the present invention into this disc space provides a simple means of maintaining the desired disc space and motion, potentially improving a long term surgical outcome.

In addition to wall thickness, and as noted above, other design parameters can be taken into account to provide an implant meeting specific needs of a patient. For example, by varying the height of the first end 101 relative to the second end 100, the angle of the implant upper section 102 changes relative to the lower section 103. This allows the implant to be manufactured in various lordotic angles to match specific patient geometric requirements. It also allows the implant to be manufactured in various heights and widths. Depending on the surgical approach, either one larger implant, such as that shown in FIG. 9, or two smaller implants, such as shown in FIGS. 1 through 8, can be used for stabilization and restoration of the affected disc space.

In a preferred embodiment, two separate implants are inserted from the posterior aspect of the spine. This provides for easier insertion, as smaller implants allow access to the disc space without disturbing the lamina or facet joints. Once implanted, the two separate implants function in tandem.

Figure 9:
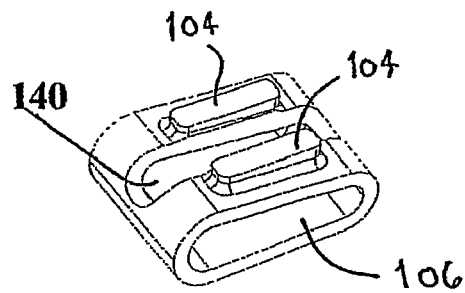
FIG. 9 is a perspective view of a larger embodiment of the present invention.

The implant and implant system described can have multiple variations. First, a large, single implant can be used for anterior, anterior-lateral, or lateral insertion. As shown in FIG. 9, for example, such an implant may have grooves or slots 140 in the surface to reduce implant stiffness. Secondly, two implants can be used to form the means of restoring motion and disc height. These implants would be smaller than a single implant for ease in insertion. In addition, the surface or surfaces of the implant directly in contact with the end plates of adjacent vertebrae can be textured to allow enhanced bone attachment or bone ingrowth. The implants can be completely smooth, or completely textured, polished via electropolishing, glass beaded, or finished in other ways to provide a fatigue resistant implant. Alternatively, partial sections of the implant can be textured, porous coated, or treated in a manner to assist in bone ingrowth for areas in contact with the vertebral end plates. Shot peening may also be used to increase fatigue life with certain materials.

Figure 6:
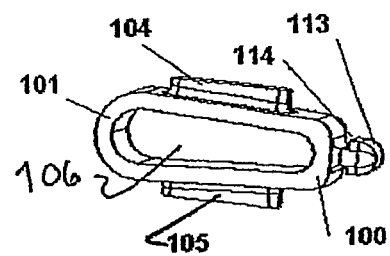
FIG. 6 is a perspective view of an embodiment of the present invention with a tab type attachment means.
Figure 7:
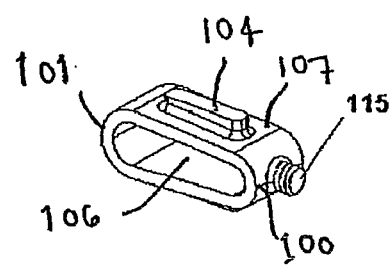
FIG. 7 is a perspective view of an embodiment of the present invention with a thread type attachment means.
Figure 10:
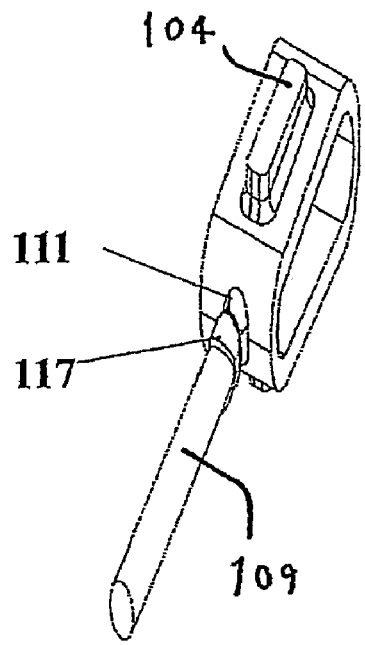
FIG. 10 is a perspective view of an embodiment of the present invention showing a bayonet connection means aligned with the instrument.
Figure 11:
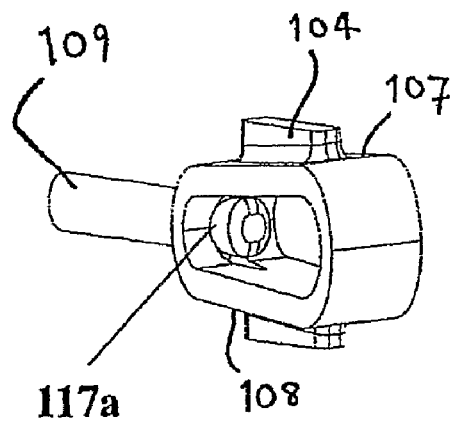
FIG. 11 is a perspective view of the embodiment shown in FIG. 10 with the bayonet connection means engaged with the instrument.

Moving now to the method and system for insertion, it is noted that means for attachment to an insertion or removal instrument can be provided on the implant itself. For example, there can be an instrument receiving hole 111 in the implant, as shown in the embodiment illustrated in FIG. 5. In an alternative embodiment, there could be provided an extension, such as a threaded post 115 or grooved tab 113, as shown in FIGS. 7 and 6, respectively. FIGS. 10 and 11 show an exemplary implant disposed on the distal end portion 109 of an insertion instrument (discussed in more detail below). It is also possible to hold onto the side of the implant and not have such a feature; however, a feature that allows implantation or removal of the implant with an instrument that does not exceed the width of the implant is typically advantageous.

Figure 12:
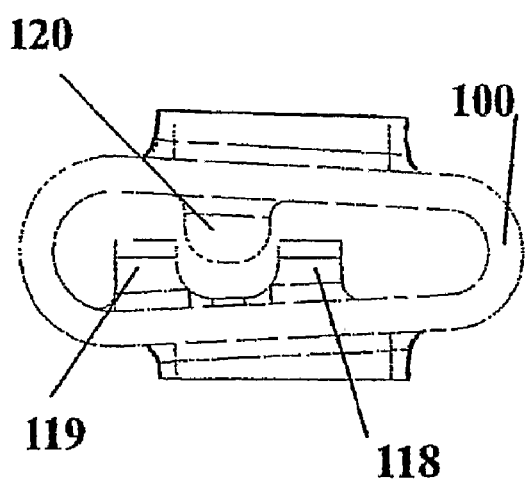
FIG. 12 is a side view of an embodiment of the present invention with an internal locking mechanism.
Figure 13:
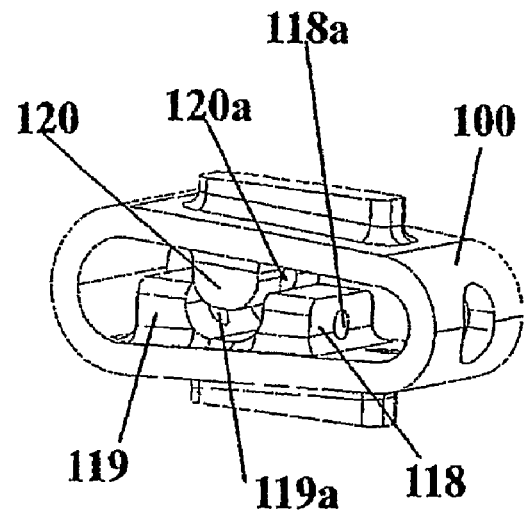
FIG. 13 is a perspective view of the embodiment shown in FIG. 12.
Figure 14:
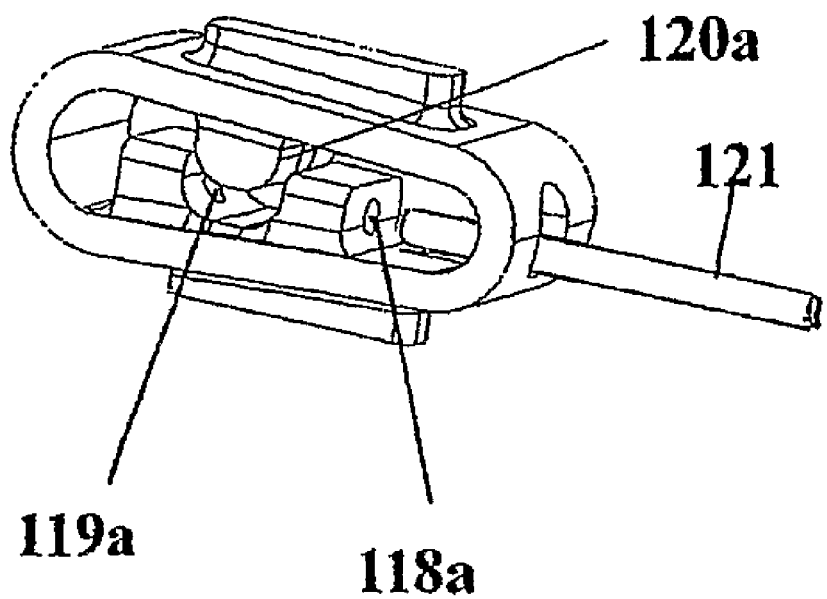
FIG. 14 is a perspective view of an embodiment of the present invention with the internal locking mechanism and locking instrument partially inserted.
Figure 15:
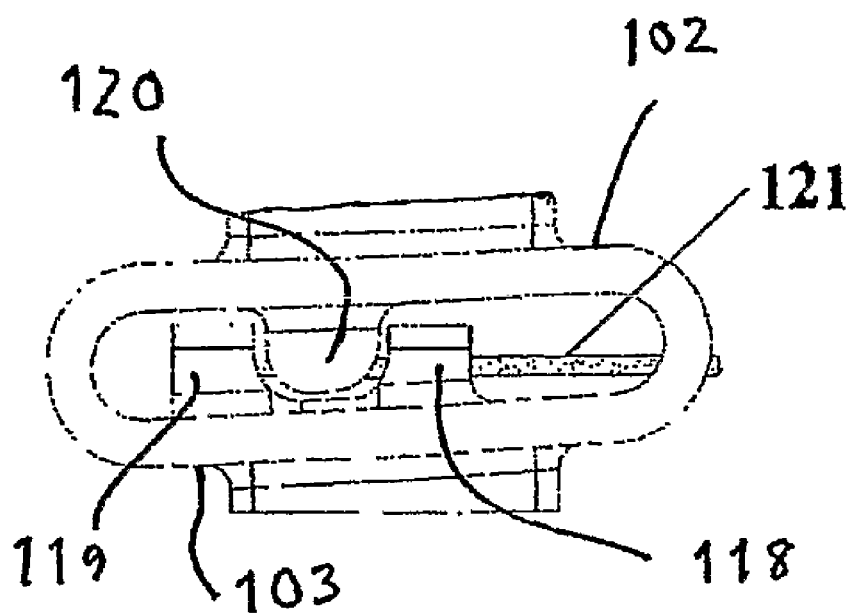
FIG. 15 is a side view of an embodiment of the present invention with the internal locking mechanism and locking instrument engaged.

In one embodiment, an internal feature is created as a part of the implant to aid in insertion. As shown in FIGS. 12 and 13, such an implant has extensions disposed into passageway 106 which oppose each other. In a preferred such embodiment, upper section extension 120 extends from the inner surface of upper section 102 toward lower section 103, and two lower section extensions 118, 119 extend upward toward upper section 102 from the upper surface of lower section 103. These protrusions interact such that they can be engaged to lock the implant in a reduced size. This allows for the ability to keep the implant at a reduced profile for insertion in difficult access points, such as in the posterior spine. Specifically, and as shown in FIGS. 13, 14, and 15, holes 118a, 119a, 120a can be aligned and a locking device inserted therethrough such as is shown in FIG. 14. The device for insertion will be addressed in more detail below. Moreover, however, rod 121 extending distally from an insertion tool (the entire tool not being shown in FIGS. 14 or 15) can engage the holes in the protrusions to thus hold the implant in a reduced profile. FIG. 15 shows the rod in place to hole the implant in its reduced profile, and FIG. 14 shows the implant expanded to its relaxed state after rod 121 has been pulled proximally out of the holes of the anchoring protrusions.

As indicated above, the implant of the present invention can be manufactured from various materials having the requisite elasticity and strength requirements. Materials such as titanium alloys, including, but not limited to Ti-6Al-4V, Ti—Mo, and memory shape alloys such as Nickel-Titanium (NiTi) can be used. In addition, biocompatible polymers or reinforced polymers can be used. For healing of the nucleus, it may be advantageous to use a bioresorbable material that would allow temporary support and motion and then be resorbed over time. The shape of the implant is preferably angled relative to the upper and lower sections to restore normal spine lordotic angle. However, other shapes, such as an oval whereby the upper and lower sections are parallel, can be constructed to meet anatomic or other requirements.

Manufacturing of the implant requires normal machining or forming techniques known in the industry. One technique is to machine the outer and inner profiles on a milling machine using proper size tooling and fixtures. Another method is to mill the outside profile and cut the inside surfaces using an EDM, or Electrical Discharge Machining technique whereby a wire cuts by use of large electrical currents. Still another newer technique is by cutting one or more surfaces by use of a laser. Obviously, multiple techniques can be combined to machine the device and surfaces. For example, the outside profile can be milled by use of a CNC mill with a ball nose end mill, which allows cutting the fins or protrusions while maintaining a blend radius around the features to minimize stress concentrations. The inside profile can be cut using the wire EDM, and the flat surfaces textured by use of a laser or chemical milling technique. Other surface enhancements, such as polishing, sand blasting, shot peening, glass beading, and other treatments are well known in the industry.

As noted above, protrusions can extend from one or more outer surfaces of the implant to contact adjacent vertebrae. Such protrusions can have a cutting feature to eliminate bone preparation for receiving said extensions, or be smooth. When an extension is smooth, a preparation instrument can be used to cut an opening or openings in the bone for receiving the extensions. In addition, it is possible to manufacture the device such that the extensions are retractable or collapsible to provide a reduced height for insertion. After insertion, these extensions are allowed to return to the desired dimension for engagement of the vertebral end plates.

Figure 16A:
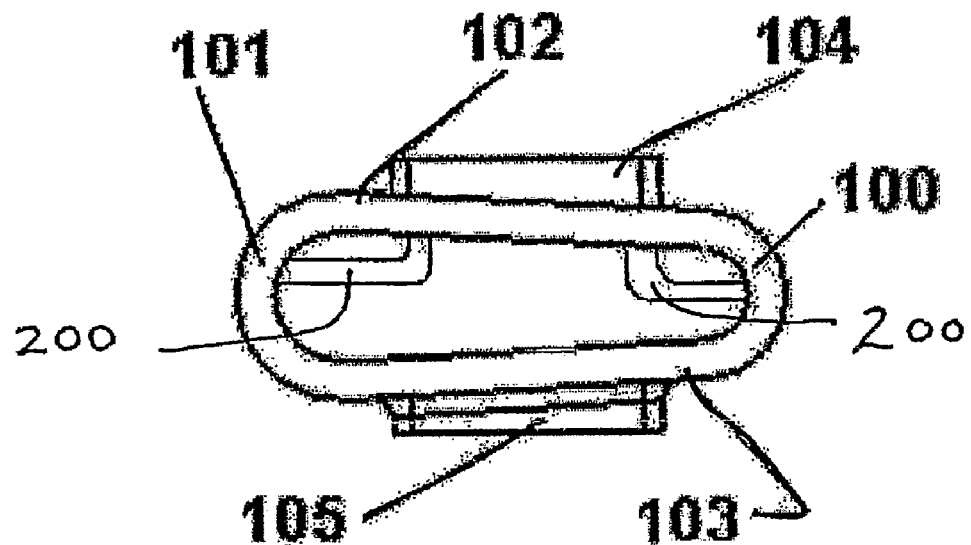
FIG. 16A illustrates an embodiment where a protrusion is mounted on flexible extensions.
Figure 16B:
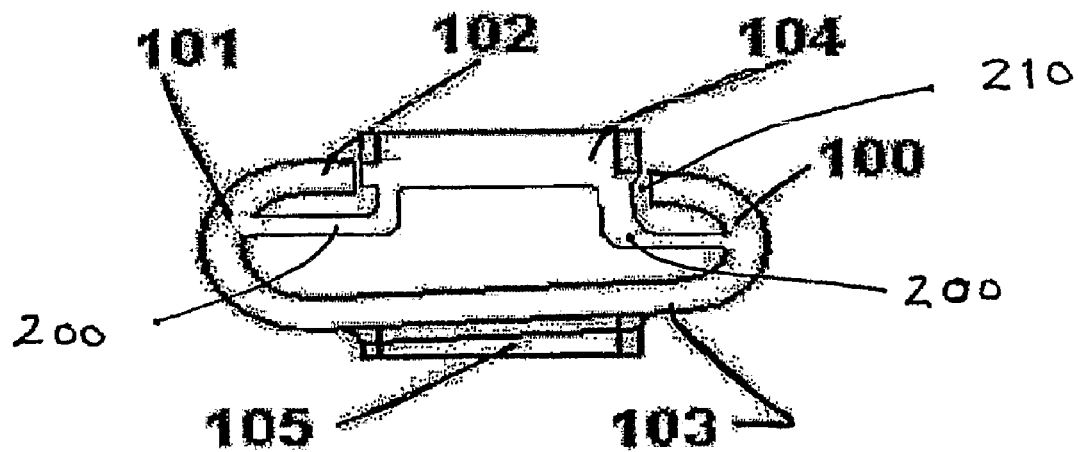
FIG. 16B illustrates a cross section of the embodiment of FIG. 16A, along the opening that allows the protrusion to extend through the upper wall of the implant.

FIGS. 16A and 16B show an embodiment where protrusion 104 is mounted on flexible extensions 200, instead of directly to the top of the implant as in the embodiments described above. In this embodiment, protrusion 104 extends through the upper section 102 of the implant through hole 210. Flexible extensions 200 may be formed integrally with the implant according to the manufacturing techniques described herein. Specifically, the flexible arms in this embodiment are attached to the inner surfaces of first and second ends 101 and 100. This embodiment works such that protrusion 104 is free to compress or expand apart from upper section 102 of the implant. As can be seen in FIG. 16B, an opening, or hole 210, is formed in part of the upper section 102 to accommodate protrusion 104 being connected to flexible arms 200. As protrusion 104 is compressed downward into the implant, flexible arms 200 transfer the compressive force to the ends 100 and 101, only to return the protrusion 104 to its upward, at-rest position when the compressive force is removed. This feature allows for the compression of protrusion 104 to a compressed state during insertion, without having to compress the entire implant in order to achieve a reduced profile for insertion.

To accommodate different patients, and different parts of a patient, different sizes of the implant are possible, including implants having different heights and widths along with multiple angles. This allows a surgeon the choice to match patient specific requirements. Matching these features along with the material thickness and properties, provides the potential for an infinite number of combinations to fine tune the implant to the needs of the patient.

As noted above, the present invention includes a method of treating a spine, comprising the steps of providing a vertebral implant, the implant having a wall forming two short sides and two elongated sides to define a generally elongated structure having a passageway therethrough and at least one of the two elongated sides being resiliently compressible into the passageway, or resiliently expandable away from the passageway, under a force applied to the implant by movement of the spine into which the implant is placed, the at least one side returnable to an at-rest position when the force is removed. The method includes the steps of compressing the implant by applying a compressive force against at least one of the elongated sides, placing the implant between two adjacent vertebrae, and releasing the compressive force to thereby allow the implant to expand between the two adjacent vertebrae.

Figure 4:
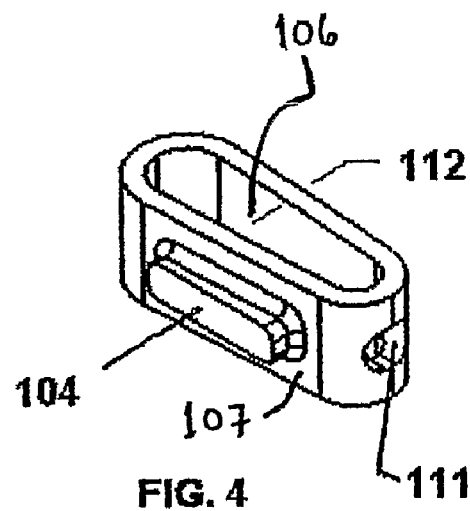
FIG. 4 is a perspective view of the embodiment shown in FIG. 2.

FIGS. 17-19 illustrate an insertion instrument and its use to deploy an implant in accordance with the present invention. Specifically, the insertion instrument can attach to the implant by insertion of the distal end 117 of the insertion instrument. The distal end 117 as shown in FIGS. 10 and 11, as well as FIG. 17, for example, is inserted into an elongated groove or hole 111 in the implant. FIGS. 2-4 also show groove or hole 111. In this embodiment, hole 111 has a height and a width which are unequal in dimension. For example, the hole can have a height that is greater than the width. The end of the instrument, namely distal end 117, also has a width and height whereby the instrument tip will only slide into the implant in a manner that aligns the height and width of the instrument tip to the same dimensions of the hole 111, namely that the orientation of the two are insertably compatible. This creates a bayonet type effect which, upon rotation of the instrument tip with respect to the implant (i.e., the implant can rotate, too, with respect to the tip), preferably ninety degrees, the instrument tip will engage the inner surface of the wall of the implant, thus allowing secure locking of the instrument to the implant.

An alternative means of attachment would include an extended tab 113 with a groove or undercut 114, as shown in FIG. 6. An instrument having a portion designed to engage the tab and groove, undercut, or other feature will allow secure locking of the implant to the instrument. Another means of attachment would include the provision of a threaded extension 115 (as shown in FIG. 7) such that an instrument can be threaded onto the threaded extension to allow secure locking of the implant to the instrument.

A preferred instrument is designed to be compatible with the embodiments discussed above with respect to FIGS. 12-15. Such an instrument is shown in FIGS. 17-19, and has a handle portion 122 with a tube section 124 having a distal portion opening to receive the implant, beginning with its second end 100 in accordance with the attachment means noted above. Moreover, shaft 125 securely locks to the implant. The tube opening is smaller than the expanded (at-rest) dimension of the first end 101 of the implant. By squeezing the handle 122 with respect to trigger 123, the trigger pivots on trigger pin 127, and the implant is drawn into the tube 124 and compressed to a smaller size. As can be seen in FIG. 18, slot 128 in tube 124 is provided to receive bone anchor protrusion 104. In an alternative embodiment, the bone contacting protrusions could also be brought within tube 124.

Slider controller 126 on the instrument allows directional control of the shaft 125 such that after the implant is inserted into the disc space, the slider direction can be changed to allow the instrument to force the implant distally out of the tube 124. As the implant is elastic, it will naturally spring back to its original shape as it is deployed, as shown in FIG. 19. FIG. 19 illustrates deployment of a device of the present invention between two adjacent vertebrae 120 and 131. Once seated between the upper vertebral body 130 and lower vertebral body 131, the implant is slowly released from the instrument and allowed to return to its original shape 150 or neutral position, as shown in FIG. 19.

The device described functions in a manner that allows ease of insertion into a disc space, maintenance or restoration of the proper disc space, and motion of the affected disc. Under sufficient load, the upper implant section will move toward the lower implant section. Upon release of the load, the implant will return to its original height. This creates a spring-like effect that allows the implant to expand and collapse in varying ways according to the applied load. Resting condition, or lack of load sufficient to cause alteration of the dimensions of the implant, allows for restoration of the proper disc space and is effectively the neutral position. For example, an implant having a first end larger than the second end is implanted such that the first end is placed anteriorly in the spine. The size is chosen based on what the normal healthy disc space should be along with the correct lordotic angle. This restores the proper disc height and removes pressure from the nerve roots and facet joints. It is this initial positioning that creates the neutral position. Under physiological loading, this implant can move in complex motions. Pure anterior flexion of the spine transfers load to the front portion of the implant. This load causes the implant shape to change. The upper and lower sections move towards each other, causing an alteration to the lordotic angle as well as other dimensional changes. This shape change effectively recreates motion. By maintaining the loads within the elastic range of the material, the implant will return to the neutral position upon release of the loading condition.

Other motions, such as medial-lateral flexion are also allowed. This side to side loading also causes the implant to change shape, thereby allowing motion of the vertebral bodies. With the use of two implants, such as that which would be preferred for a posterior approach where access to the spine is limited, the two implants share loading. It is possible to have one implant relatively unloaded and the other implant loaded depending on the motion of the spine. It should be noted that there is always compressive load on the implant due to weight, ligaments, and muscles.

The same features that allow motion of the implant also allow collapse of the implant for insertion and expansion of the implant back to the original height after insertion. This provides an advantage, as it is easier to insert a smaller implant. Thus, the implant can be compressed with an instrument and held in a reduced height configuration until properly seated in the disc space.

For enhancement of adhesion or bone ingrowth to the implant bone contact surfaces, the surfaces can treated to allow surface roughness or porosity. This surface roughness can be provided by blasting, machining, chemical etching, laser treating, porous coating, or other means. In addition, coatings can be used to enhance bone growth. Hydroxyapatite, calcium sulfate, Bone Morphogenetic Proteins (BMP), and other surface treatments are examples of applied bone enhancing substances.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Although the present invention has been particularly described in conjunction with specific preferred embodiments, it is evident that many alternatives, modifications, and variations will be apparent to those skilled in the art. It is therefore contemplated that the appended claims will embrace any such alternatives, modifications, and variations as falling within the true scope and spirit of the present invention.

What is claimed:

1. A vertebral implant comprising:
    a wall forming two short sides and two elongated sides to define a generally elongated structure having a passageway therethrough; and
    at least one of said two elongated sides being resiliently compressible into said passageway under a force applied to the implant by movement of the spine into which the implant is placed,
    one of the two elongated sides comprising first and second anchoring projections extending into the passageway, and the other of the two elongated sides comprising a third anchoring projection extending into the passageway, said anchoring projections engageable to secure the implant in a reduced profile configuration in which the third anchoring projection extends into the passageway between the first and second anchoring projections,
    said at least one elongated side returnable to an at-rest position when the force is removed,
    wherein the anchoring projections each have a hole, the holes aligned when the implant is in the reduced profile configuration to form a single passage for receiving a single rod to hold the implant in said reduced profile configuration.

2. The vertebral implant of claim 1 wherein the two short sides are rounded and the two elongated sides are straight, said sides defining a generally elongated loop-shaped implant.

3. The vertebral implant of claim 1 wherein one of the two short sides is larger than the other short side, said larger side forming an anterior end of the vertebral implant.

4. The vertebral implant of claim 1 further comprising a bone contacting protrusion extending from an outer surface of at least one of the elongated sides in a direction away from the passageway.

5. The vertebral implant of claim 4 wherein the bone contacting protrusion is elongated.

6. The vertebral implant of claim 1 further comprising wherein the wall forms a hole to receive a portion of an insertion tool.

7. The vertebral implant of claim 1 wherein the implant is made from a titanium alloy.

8. The vertebral implant of claim 1 wherein the implant is made from a biocompatible polymer.

9. The vertebral implant of claim 1 wherein the implant is made from a biocompatible, bioresorbable polymer.

10. A vertebral implant comprising:
    a wall forming a two rounded sides and two elongated straight sides to define a generally elongated structure having a passageway therethrough, one rounded short side being larger than the other rounded short side whereby the two elongated straight sides are not parallel; and
    at least one of said two elongated sides being resiliently compressible into said passageway under a force applied to the implant by movement of the spine into which the implant is placed;
    one of the two elongated sides comprising first and second anchoring projections extending into the passageway, and the other of the two elongated sides comprising a third anchoring projection extending into the passageway, said anchoring projections engageable to secure the implant in a reduced profile configuration in which the third anchoring projection extends into the passageway between the first and second anchoring projections,
    said at least one elongated side returnable to an at-rest position when the force is removed,
    wherein the anchoring projections each have a hole, the holes aligned when the implant is in the reduced profile configuration to form a single passage for receiving a single rod to hold the implant in said reduced profile configuration.

11. The vertebral implant of claim 10 further comprising a bone contacting protrusion extending from an outer surface of at least one of the elongated sides in a direction away from the passageway.

12. The vertebral implant of claim 11 wherein the bone contacting protrusion is elongated.

13. The vertebral implant of claim 10 further comprising wherein the wall forms a hole to receive a portion of an insertion tool.

14. The vertebral implant of claim 10 wherein the implant is made from a titanium alloy.

15. The vertebral implant of claim 10 wherein the implant is made from a biocompatible polymer.

16. The vertebral implant of claim 10 wherein the implant is made from a biocompatible, bioresorbable polymer.

17. A method of treating a spine, comprising the steps of:
    providing a vertebral implant, the implant having:
    a wall forming two short sides and two elongated sides to define a generally elongated structure having a passageway therethrough, one of the two elongated sides comprising first and second anchoring projections extending into the passageway, and the other of the two elongated sides comprising a third anchoring projection extending into the passageway, said anchoring projections engageable to secure the implant in a reduced profile configuration in which the third anchoring projection extends into the passageway between the first and second anchoring projections;
    at least one of the two elongated sides being resiliently compressible into the passageway under a force applied to the implant by movement of the spine into which the implant is placed, the at least one elongated side returnable to an at-rest position when the force is removed;
    compressing the implant by applying a compressive force against at least one of the elongated sides;
    placing the implant between two adjacent vertebrae; and
    releasing the compressive force to thereby allow the implant to expand between the two adjacent vertebrae,
    wherein the anchoring projections each have a hole, the holes aligned when the implant is in the reduced profile configuration to form a single passage for receiving a single rod to hold the implant in said reduced profile configuration.

18. The method of claim 17 further comprising the step of releasably attaching the implant to the distal end of a delivery device before the placing step.

19. A method of treating a spine, comprising the steps of:
    providing a vertebral implant, the implant having:
    a wall forming two short sides and two elongated sides to define a generally elongated structure having a passageway therethrough, one of the two elongated sides comprising first and second anchoring projections extending into the passageway, and the other of the two elongated sides comprising a third anchoring projection extending into the passageway, said anchoring projections engageable to secure the implant in a reduced profile configuration in which the third anchoring projection extends into the passageway between the first and second anchoring projections;
    at least one of the two elongated sides being resiliently compressible into the passageway under a force applied to the implant by movement of the spine into which the implant is placed, the at least one elongated side returnable to an at-rest position when the force is removed;

releasably attaching the implant to the distal end of an insertion tool;

retracting the implant into a shaft of the insertion tool to thereby compress the implant to a contracted state;

placing the implant between two adjacent vertebrae; and releasing the compressive force to thereby allow the implant to expand between the two adjacent vertebrae, wherein the anchoring projections each have a hole, the holes aligned when the implant is in the reduced profile configuration to form a single passage for receiving a single rod to hold the implant in said reduced profile configuration.

\* \* \* \* \*